United States Patent
Liu et al.

(10) Patent No.: US 10,768,321 B2
(45) Date of Patent: Sep. 8, 2020

(54) X-RAY DETECTOR COOLING SYSTEM AND X-RAY IMAGING SYSTEM

(71) Applicant: GENERAL ELECTRIC COMPANY, Schenectady, NY (US)

(72) Inventors: Hailiang Liu, Beijing (CN); Min Zhou, Beijing (CN); Sen Wang, Beijing (CN); Yefu Li, Beijing (CN)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 16/222,655

(22) Filed: Dec. 17, 2018

(65) Prior Publication Data
US 2019/0187308 A1    Jun. 20, 2019

(30) Foreign Application Priority Data

Dec. 15, 2017   (CN) .......................... 2017 1 1349622

(51) Int. Cl.
| | | |
|---|---|---|
| *H05G 1/00* | (2006.01) | |
| *G01T 7/00* | (2006.01) | |
| *F25B 41/00* | (2006.01) | |
| *G01T 1/29* | (2006.01) | |
| *F25D 19/00* | (2006.01) | |
| *A61B 6/00* | (2006.01) | |
| *F25B 21/02* | (2006.01) | |

(52) U.S. Cl.
CPC .............. *G01T 7/00* (2013.01); *A61B 6/4488* (2013.01); *F25B 41/003* (2013.01); *F25D 19/006* (2013.01); *G01T 1/2985* (2013.01); *F25B 21/02* (2013.01)

(58) Field of Classification Search
CPC ....... G01T 7/00; G01T 1/2985; F25B 41/003; F25B 21/02; F25D 19/006; A61B 6/4488
See application file for complete search history.

(56) References Cited

U.S. PATENT DOCUMENTS 6,669,366 B2 * 12/2003 Busse .................... A61B 6/035
378/199
2017/0059720 A1 * 3/2017 McBroom ............. G01T 1/2985

\* cited by examiner

*Primary Examiner* — Kiho Kim (57) ABSTRACT

Provided are a cooling system with no refrigeration machine for an X-ray detector, and an X-ray imaging system using the system. The cooling system for an X-ray detector comprises: a cooling pipeline positioned on an X-ray detector; and a coolant transfer pipeline positioned at least partially in a support device of the X-ray detector and connected with the cooling pipeline to form a circulation loop, the circulation loop being provided with a circulating coolant therein. On the basis of the existing X-ray photography system, the configuration of a refrigeration machine can be removed from the cooling system, and the cooling of the detector can be realized with as few changes as possible, while meeting the temperature requirements of the normal operation of the detector and reducing costs.

8 Claims, 6 Drawing Sheets

X-RAY DETECTOR COOLING SYSTEM AND X-RAY IMAGING SYSTEM

FIELD OF THE INVENTION

The present invention relates to a cooling system for an X-ray detector, and an X-ray imaging system having the cooling system for an X-ray detector.

BACKGROUND OF THE INVENTION

An X-ray imaging system usually comprises an X-ray bulb tube, an X-ray detector and a support device, such as a C-shaped arm, which supports the X-ray bulb tube and the X-ray detector. During operation, an imaging platform, on which a patient is located, is located between the X-ray bulb tube and the X-ray detector. X-rays emitted from the X-ray bulb tube pass through the patient on the imaging platform and are received by the X-ray detector. As the rays pass through the patient, the anatomical structure of the patient's body causes a spatial change in the radiation received at the X-ray detector. The X-ray detector then converts this radiation change into an image that can be used for clinical assessment.

Some application procedures, such as an interventional procedure, require a relatively long imaging cycle in order to correctly diagnose, treat, and/or assess the patient's condition. Working for a long time will cause the X-ray detector to generate a large amount of heat, and the temperature range of the X-ray detector is relatively strict. In the prior art, most manufacturers equip the X-ray detector with a refrigeration machine, which is connected to a detector module via two hoses and strictly controls the detector such that same works within an appropriate temperature range. The X-ray imaging system is installed in an examination room, and considering the limited space in the examination room, the refrigeration machine is installed in an equipment room, and the hose connected between the two is thus 18 to 24 meters long. The refrigeration machine not only increases hardware costs, but also increases daily expenses, and dozens of meters of wiring is also not convenient during installation. Therefore, there is a need to propose a cooling system with no refrigeration machine for an X-ray detector, in order to realize the cooling of the X-ray detector by using existing components as much as possible.

BRIEF DESCRIPTION OF THE INVENTION

An object of the present invention is to provide a cooling system with no refrigeration machine.

According to an aspect of the present invention, provided is a cooling system for an X-ray detector, the cooling system comprising:

a cooling pipeline positioned on an X-ray detector; and a coolant transfer pipeline positioned at least partially in a support device of the X-ray detector and connected with the cooling pipeline to form a circulation loop, the circulation loop being provided with a circulating coolant therein.

Preferably, the cooling system for an X-ray detector further comprises a pump for driving the coolant to circulate, and a coolant replenishing device positioned in the circulation loop.

Preferably, the support device comprises a C-shaped arm, and a first section of the coolant transfer pipeline is embedded into the C-shaped arm.

Preferably, at least one surface of the C-shaped arm is provided with a groove, the first section of the coolant transfer pipeline is embedded into the groove, and a gap between the groove and the first section of the coolant transfer pipeline is filled with a highly thermally conductive material.

Preferably, the cooling system for an X-ray detector further comprises a coolant replenishing device positioned in the circulation loop, wherein the coolant replenishing device comprises a first chamber and a second chamber, the first chamber is connected to the coolant transfer pipeline, and the second chamber is connected to the first chamber via a connection pipe, and when the coolant replenishing device is tilted at a specific angle, the first chamber is full of the coolant, and the liquid level of the coolant in the second chamber is higher than the position of the connection pipe.

Preferably, the specific angle is not greater than the maximum rotation angle of the C-shaped arm.

Preferably, the support device comprises a support base, and a second section of the coolant transfer pipeline is mounted in the support base.

Preferably, the cooling system for an X-ray detector further comprises a heat dissipation pipeline mounted on an inner wall of the support base, the heat dissipation pipeline being connected in series in the second section of the coolant transfer pipeline.

Preferably, the heat dissipation pipeline comprises a plurality of heat exchangers which are arranged in a matrix.

Preferably, the heat dissipation pipeline comprises a curved pipe.

According to another aspect of the present invention, provided is an X-ray imaging system, which comprises an X-ray detector, a support device for supporting the X-ray detector, and a cooling system for the X-ray detector, wherein the cooling system comprises: a cooling pipeline positioned on an X-ray detector; and a coolant transfer pipeline positioned at least partially in a support device of the X-ray detector and connected with the cooling pipeline to form a circulation loop, the circulation loop being provided with a circulating coolant therein.

Preferably, the cooling system for an X-ray detector further comprises a pump for driving the coolant to circulate, and a coolant replenishing device positioned in the circulation loop.

Preferably, the support device comprises a C-shaped arm, and a first section of the coolant transfer pipeline is embedded into the C-shaped arm.

Preferably, at least one surface of the C-shaped arm is provided with a groove, the first section of the coolant transfer pipeline is embedded into the groove, and a gap between the groove and the first section of the coolant transfer pipeline is filled with a highly thermally conductive material.

Preferably, the coolant replenishing device further comprises a coolant replenishing device positioned in the circulation loop, wherein the coolant replenishing device comprises a first chamber and a second chamber, the first chamber is connected to the coolant transfer pipeline, and the second chamber is connected to the first chamber via a connection pipe, and when the coolant replenishing device is tilted at a specific angle, the first chamber is full of the coolant, and the liquid level of the coolant in the second chamber is higher than the position of the connection pipe.

Preferably, the specific angle is not greater than the maximum rotation angle of the C-shaped arm.

Preferably, the support device comprises a support base, and a second section of the coolant transfer pipeline is mounted in the support base.

Preferably, the cooling system for an X-ray detector further comprises a heat dissipation pipeline mounted on an inner wall of the support base, the heat dissipation pipeline being connected in series in the second section of the coolant transfer pipeline.

Preferably, the heat dissipation pipeline comprises a plurality of heat exchangers which are arranged in a matrix.

Preferably, the heat dissipation pipeline comprises a curved pipe.

BRIEF DESCRIPTION OF THE DRAWINGS

The present invention will be better understood by the description of two embodiments of the present invention in conjunction with the accompanying drawings, in which.

DETAILED DESCRIPTION OF THE INVENTION

Unless defined otherwise, technical or scientific terms used herein should be interpreted in the ordinary sense as understood by those of ordinary skill in the art to which this invention pertains. The terms "first", "second" and the like used in the description and the claims in the present invention are merely used to distinguish different components, rather than denoting any order, quantity, or importance. Likewise, the term "a" or "an" or the like also denotes the presence of at least one, rather than representing a quantitative restriction. The term "comprising" or "including" or the like means that the element or object before the term "comprising" or "including" encompasses the element or object or equivalent listed after the term "comprising" or "including", without excluding other elements or objects.

The present invention provides a cooling system with no refrigeration machine for an X-ray detector. On the basis of the existing X-ray imaging system, the configuration of a refrigeration machine can be removed from the cooling system, and the cooling of the detector can be realized with as few changes as possible, while meeting the temperature requirements of the normal operation of the detector and reducing costs.

Figure 1:
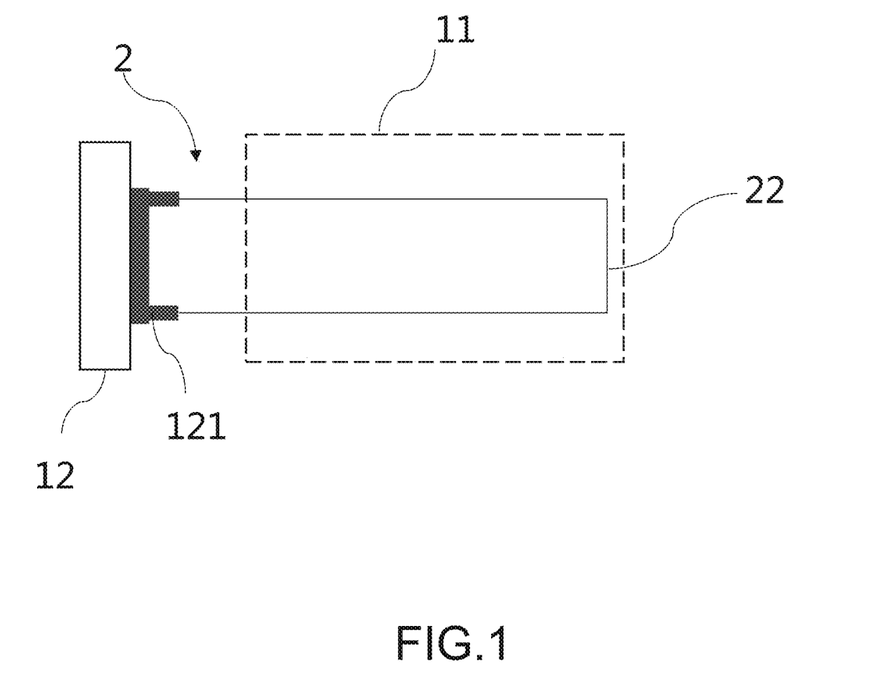
FIG. 1 shows a structural schematic diagram of a cooling system for an X-ray detector according to an embodiment of the present invention.

FIG. 1 shows a schematic diagram of a cooling system 2 for an X-ray detector according to an embodiment of the present invention. Currently, X-ray detectors on the market are provided with cooling pipelines and external interfaces for future use. A cold plate is arranged on the back of a detector 12, a groove is formed on the cold plate, and a cooling pipeline 121 is embedded into the groove. The cooling pipeline 121 is provided with a water inlet and a water outlet for future use. In the existing refrigeration system, a refrigeration machine is connected to the water inlet and the water outlet respectively via hoses. The heat generated by the X-ray detector 12 is thermally conducted to the cooling pipeline through the cold plate. The cooling pipeline contains a refrigerant, which is refrigerated by the refrigeration machine and is precisely controlled within a certain temperature range, so as to ensure that the temperature of the X-ray detector is within a normal working range (such as not more than 3° C.). The refrigeration machine is generally based on the principle of a thermoelectric cooler (TEC).

The present invention provides a design concept, i.e. instead of active cooling by virtue of the refrigeration machine, a new coolant transfer pipeline 22 is designed to take away the heat generated by the X-ray detector by circulating a coolant in the coolant transfer pipeline.

As shown in FIG. 1, the present invention retains the cooling pipeline 121 of the original X-ray detector 12, the water inlet and the water outlet of the cooling pipeline 121 are respectively connected to the coolant transfer pipeline 22, and the coolant transfer pipeline 22 and the original cooling pipeline 121 form a circulation loop. In this embodiment, the coolant transfer pipeline 22 may still use a plastic hose. In some embodiments, a metal tube may be sheathed outside the hose to increase the heat dissipation efficiency.

There is a coolant circulating in the circulation loop, and the coolant may be any one selected from the prior art coolants. In this embodiment, water is used as the coolant. At least part of the pipelines of the circulation loop is installed inside a support device 11 of the X-ray detector, and the heat carried by the coolant in the circulation loop can be dissipated by the support device 11.

Figure 2:
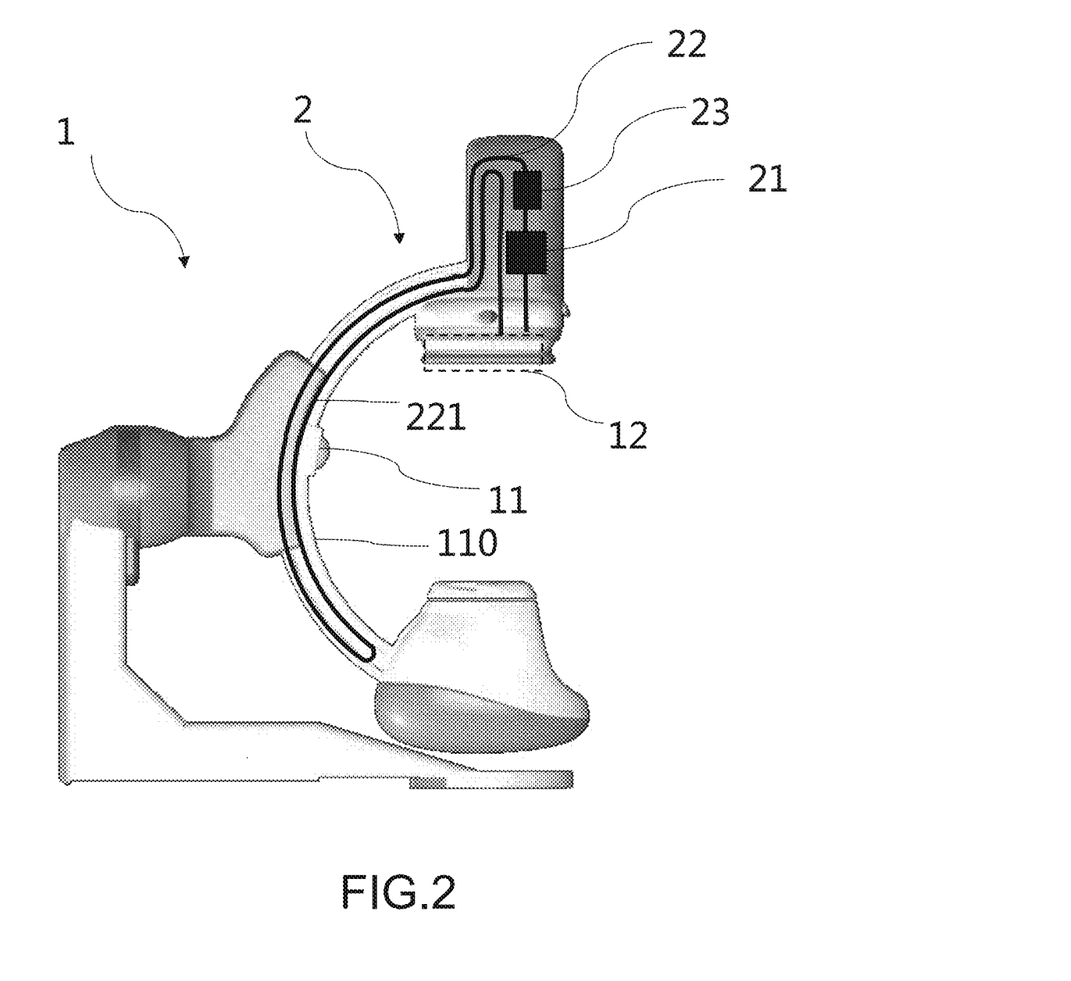
FIG. 2 shows a structural schematic diagram of an X-ray imaging system according to an embodiment of the present invention.

FIG. 2 shows a schematic diagram of an X-ray imaging system according to an embodiment of the present invention. The X-ray imaging system 1 comprises an X-ray detector 12, a support device 11 for supporting the X-ray detector, and a cooling system 2 for the X-ray detector 12. The support device 11 comprises a C-shaped arm. A cooling pipeline 121 is positioned at the back of the X-ray detector 12, a water outlet of the cooling pipeline 121 is connected to a coolant transfer pipeline 22, at least part of the coolant transfer pipeline 22 is embedded into the C-shaped arm 110, the C-shaped arm 110 is made of metal and has a good thermal conductivity, and therefore, the C-shaped arm 110 acts as a heat exchanger, thereby achieving the purpose of using the C-shaped arm to dissipate heat outwards. In this embodiment, the C-shaped arm 110 is made of aluminium.

Preferably, at least one face of the C-shaped arm 110 is provided with a groove to facilitate the installation of the coolant transfer pipeline. In this embodiment, grooves are positioned on two side faces of the existing C-shaped arm 110, the width and depth of the grooves correspond to the diameter of the coolant transfer pipeline 22, a lower half of the C-shaped arm 110 is provided with a via hole, which connects the two grooves, one pipeline section of the coolant transfer pipeline 22 is embedded into the groove on one of the side faces of the C-shaped arm and passes through the via hole, and another pipeline section is embedded in the groove on the other side face of the C-shaped arm 110, forming a U-shaped structure. At the same time, the U-shaped structure is fixed in the grooves by using metal covers matching same. Further, in some embodiments, a highly thermally conductive material, such as thermally conductive silicone, is filled between the grooves and the coolant transfer pipeline 22, so as to increase thermal conduction efficiency and also to improve the firmness.

As shown in FIG. 2, the coolant transfer pipeline 22 forms the U-shaped structure in the C-shaped arm 110, two ends of the U-shaped structure are respectively connected to the water inlet and the water outlet of the cooling pipeline 121 at the back of the X-ray detector 12, forming a circulation loop. When the X-ray imaging system works, the coolant circulates in the circulation loop, and the rotation of the C-shaped arm also increases the efficiency of circulation flow of the coolant.

Preferably, a pump 21 is connected in series in the circulation loop, and considering the limited space in a housing of the detector, a compact peristaltic pump is used in this embodiment. The peristaltic pump 21 drives the coolant to flow throughout the circulation loop to take away the heat generated by the X-ray detector 12.

In daily use, there are losses, such as evaporation, of the coolant. In order to replenish the coolant, a coolant replenishing device 23 is positioned in the circulation loop to ensure that the circulation loop is full of the coolant. In this embodiment, the coolant replenishing device 23 is installed in the housing of the X-ray detector.

As shown in FIG. 2, the housing is mounted at one end of the C-shaped arm and rotates with the C-shaped arm during operation. When the C-shaped arm is tilted, the coolant replenishing device 23 is also correspondingly tilted, and if air is present in the coolant replenishing device 23, the air may enter the circulation loop when it is tilted to a certain position, resulting in a decrease in heat dissipation capacity. Therefore, the present invention designs a coolant replenishing device which can ensure that no air enters the circulation loop when the C-shaped arm rotates.

Figure 3:
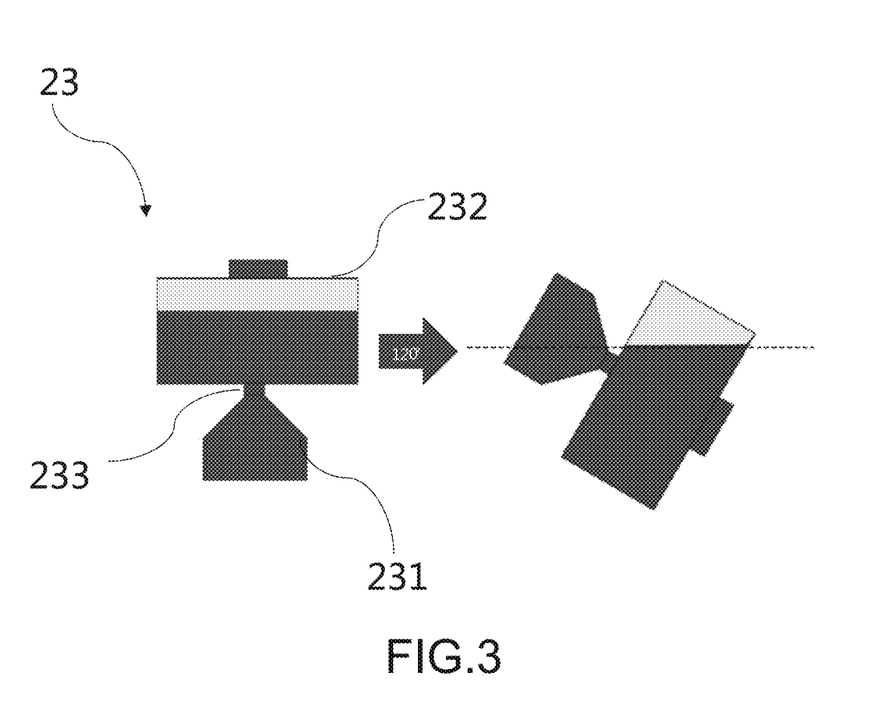
FIG. 3 shows a structural diagram of a coolant replenishing device according to an embodiment of the present invention.

FIG. 3 shows a structural schematic diagram of a coolant replenishing device according to an embodiment of the present invention in a sectional view. The coolant replenishing device 23 comprises a first chamber 231 and a second chamber 232. In this embodiment, one end of the first chamber 231 has a funnel shape, the second chamber 232 has a rectangular parallelepiped shape, and an upper end of the second chamber 232 is provided with an openable sealing cover to facilitate the daily addition of the coolant. The first chamber 231 is provided with an inlet and an outlet (not shown in the figures), and is connected in series to the coolant transfer pipeline. The first chamber 231 and the second chamber 232 are connected via a connection pipe 233, forming a "connector". The connection pipe 233 is preferably positioned in the middle of the bottom of the second chamber. When the tilt of the C-shaped arm causes the coolant replenishing device 23 to be tilted at a specific angle such as 120°, the first chamber 231 is always full of the coolant and air may exist in the second chamber 232. However, the liquid level of the coolant in the second chamber 232 is always higher than the position of the connection pipe 233, and the air thus cannot enter the circulation loop through the connection pipe 233. The maximum tilt angle of the C-shaped arm is 120°, and it can guarantee that no abnormality will occur in daily use only by ensuring, at the time of design, that no air enters the circulation loop when the coolant replenishing device in this embodiment meets the maximum tilt angle. The first chamber and the second chamber may have other shapes as long as it is ensured, based on the above principle, that the air cannot enter the connection pipe 233.

Figure 4:
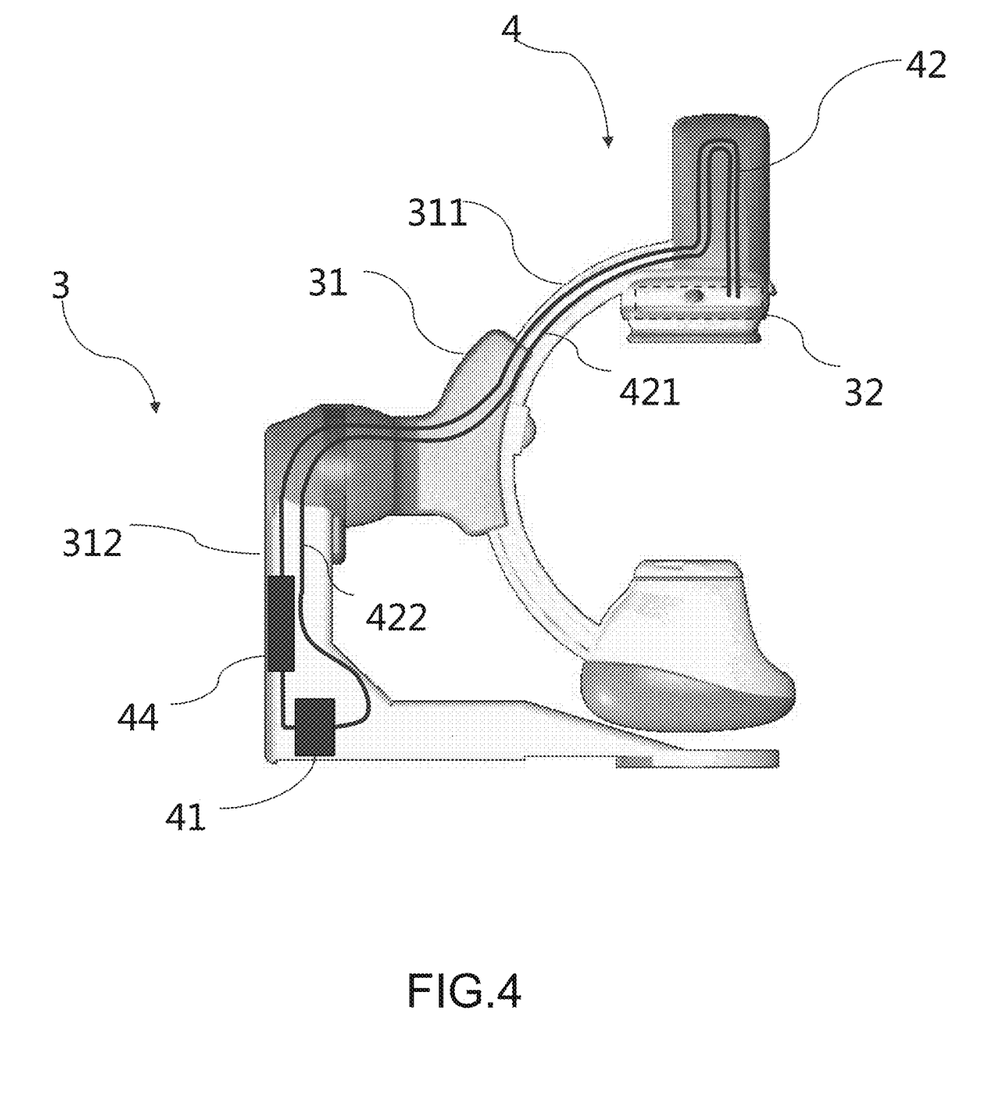
FIG. 4 shows a structural schematic diagram of an X-ray imaging system according to another embodiment of the present invention.

FIG. 4 shows a structural schematic diagram of an X-ray imaging system according to another embodiment of the present invention. The X-ray imaging system 3 comprises an X-ray detector 32, a support device 31 for supporting the X-ray detector 32, and a cooling system 4 for the X-ray detector 32. The support device 31 comprises a C-shaped arm 311 and a support base 312 for supporting the C-shaped arm. Since the support base 312 is made of metal, the design concept of this embodiment is to use the support base 312 as a heat exchanger to achieve the purpose of dissipating heat outwards through the C-shaped arm.

In this embodiment, a first pipeline section 421 of the coolant transfer pipeline 42 extends through the C-shaped arm to a second pipeline section 422, and the first pipeline section 421 may be fixed by means of a groove positioned on the C-shaped arm and may also pass through an inner space of the C-shaped arm. The second pipeline section 422 of the coolant transfer pipeline 42 is fixed in the support base 312; and one end of the coolant transfer pipeline 42 is connected to a water outlet of a cooling pipeline 321 at the back of the coolant transfer pipeline and extends through the C-shaped arm 311 and the support base 312 in succession, extends in a reverse direction from the support base, passes through the C-shaped arm 311 and finally returns to the X-ray detector 32, and is connected to the cooling pipeline 321 at the back of the coolant transfer pipeline, forming a circulation loop. The coolant circulates in the circulation loop. Preferably, a pump 41 is connected in series in the circulation loop. The coolant flows under the drive of the pump 41 and takes away the heat from the X-ray detector 32. Part of the heat is dissipated through the pipeline of the circulation loop, and the other part of the heat is dissipated through the C-shaped arm and the support base 312.

Figure 5:
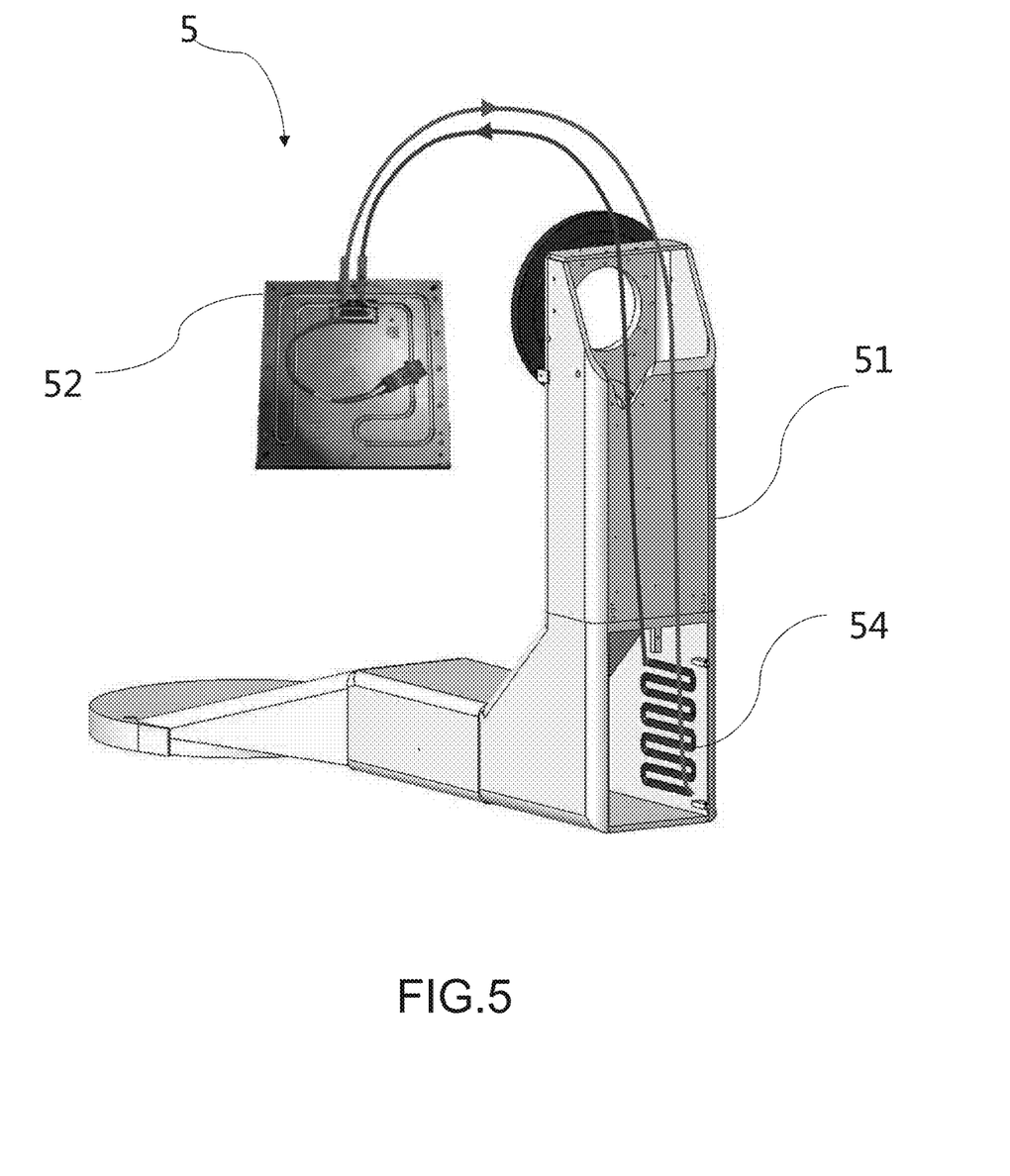
FIG. 5 shows a structural schematic diagram of a cooling system for an X-ray detector according to another embodiment of the present invention.
Figure 6:
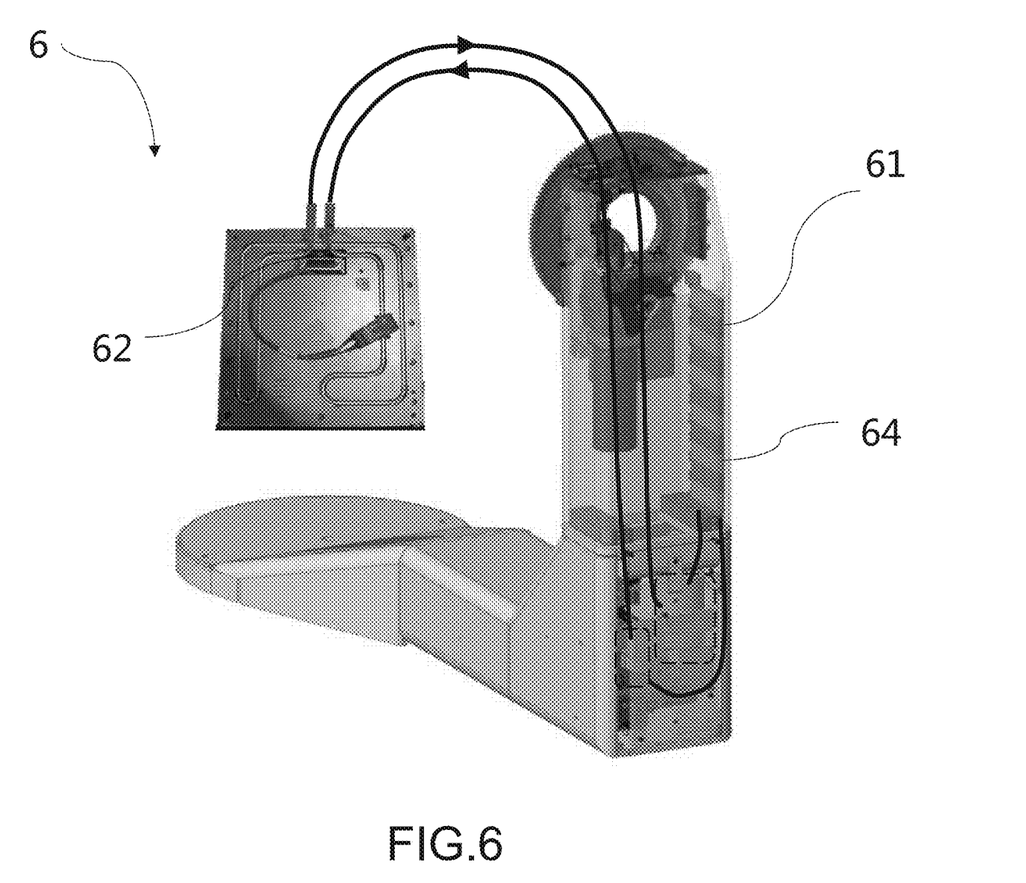
FIG. 6 shows a structural schematic diagram of a cooling system for an X-ray detector according to still another embodiment of the present invention.

Further, a heat dissipation pipeline 44 is positioned on an inner wall of the support base 312, and the heat dissipation pipeline 44 is connected in series with the second pipeline section 422, forming part of the circulation loop. When the coolant passes through the heat dissipation pipeline 44, the heat carried by the coolant is dissipated through the heat dissipation pipeline 44. FIGS. 5 and 6 show two embodiments of the heat dissipation pipeline 44 in the present invention.

As shown in FIG. 5, the heat dissipation pipeline is a curved pipe, which is made of metal, preferably copper. The curved pipe 54 increases the length of the pipeline and is fixed on a side wall of the support base 51, and the curved pipe 54 and the support base 51 together play the role of a heat exchanger. In order to improve the heat dissipation efficiency of the pipeline, the curved pipe may be made of another material and has another shape, and the design of the curved pipe belongs to the prior art and is not described in detail herein.

In another embodiment, the heat dissipation pipeline is composed of a plurality of heat exchangers 64. Each of the heat exchangers is plate-shaped and includes a water outlet and a water inlet, and the heat exchangers are connected in series in the circulation loop. The plurality of heat exchangers 64 are distributed in a matrix, and are installed on the inner wall of the support base 61, wherein adjacent heat exchangers are connected in series via hoses. As shown in FIG. 6, the plurality of heat exchangers 64 are arranged side by side on the inner wall. In some embodiments, other types of heat exchangers may be used and may be distributed in multiple rows and installed on multiple inner walls. In summary, the final design goal is to increase the heat exchange area and improve the heat dissipation efficiency.

Further, the inventor(s) has/have tested and verified the solutions shown in FIGS. 2, 4, 5 and 6. The real-time temperature of the X-ray detector is detected by a temperature sensor mounted on the X-ray detector, the experimental simulation is performed at the environment temperature of 25° C. in the operating room, and in case of the X-ray imaging system continuously running for 3 hours, the maximum temperature rise of the X-ray detector in the above solutions is only 8° C., i.e. the highest temperature of the X-ray detector is only 33° C., which completely conforms to the temperature requirements of the X-ray imaging system. The present invention makes maximum use of the existing components, meets the cooling requirements of the X-ray detector, and also reduces costs.

Although the present invention is described in conjunction with the particular embodiments, those skilled in the art will understand that many modifications and variants can be made to the present invention. Therefore, it should be recognized that the claims are intended to cover all the modifications and variants within the real conception and scope of the present invention.

We claim:

1. A cooling system for an X-ray detector, comprising:
   a cooling pipeline positioned on an X-ray detector; and
   a coolant transfer pipeline positioned at least partially in a support device of the X-ray detector and connected with the cooling pipeline to form a circulation loop, the circulation loop being provided with a circulating coolant therein; wherein the support device comprises a C-shaped arm, and wherein a first section of the coolant transfer pipeline is embedded into the C-shaped arm; and
   a coolant replenishing device positioned in the circulation loop, wherein the coolant replenishing device comprises a first chamber and a second chamber, the first chamber is connected to the coolant transfer pipeline, and the second chamber is connected to the first chamber via a connection pipe, and wherein when the coolant replenishing device is tilted at a specific angle, the first chamber is full of the coolant, and the liquid level of the coolant in the second chamber is higher than the position of the connection pipe.

2. The cooling system for an X-ray detector as claimed in claim 1, further comprising a pump for driving the coolant to circulate, and a coolant replenishing device positioned in the circulation loop.

3. The cooling system for an X-ray detector as claimed in claim 1, wherein at least one surface of the C-shaped arm is provided with a groove, wherein the first section of the coolant transfer pipeline is embedded into the groove, and wherein a gap between the groove and the first section of the coolant transfer pipeline is filled with a highly thermally conductive material.

4. The cooling system for an X-ray detector as claimed in claim 1, wherein the specific angle is not greater than the maximum rotation angle of the C-shaped arm.

5. The cooling system for an X-ray detector as claimed in claim 1, wherein the support device comprises a support base, and wherein a second section of the coolant transfer pipeline is mounted in the support base.

6. The cooling system for an X-ray detector as claimed in claim 5, further comprising a heat dissipation pipeline mounted on an inner wall of the support base, the heat dissipation pipeline being connected in series in the second section of the coolant transfer pipeline.

7. The cooling system for an X-ray detector as claimed in claim 6, wherein the heat dissipation pipeline comprises a plurality of heat exchangers which are arranged in a matrix.

8. The cooling system for an X-ray detector as claimed in claim 6, wherein the heat dissipation pipeline comprises a curved pipe.

* * * * *